United States Patent
Smith

(10) Patent No.: US 6,335,004 B1
(45) Date of Patent: *Jan. 1, 2002

(54) ODORLESS PHENOLIC COMPOSITIONS

(75) Inventor: Kim R. Smith, Woodbury, MN (US)

(73) Assignee: Ecolab Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/584,446

(22) Filed: May 31, 2000

(51) Int. Cl.[7] .............. A61K 7/08; A61K 7/00; A61K 31/05
(52) U.S. Cl. ............ 424/70.21; 424/401; 514/731; 514/737; 514/844; 514/733; 514/736
(58) Field of Search .............. 424/70.21, 70.24, 424/94.6, 401; 514/847, 94.6, 2, 731, 733, 736, 737, 844

(56) References Cited

U.S. PATENT DOCUMENTS

| 5,024,742 A | | 6/1991 | Nesburn et al. | ....... 204/157.68 |
|---|---|---|---|---|
| 5,294,314 A | | 3/1994 | Nesburn et al. | ....... 204/157.68 |
| 5,431,790 A | | 7/1995 | Nesburn et al. | ....... 204/157.68 |
| 5,490,980 A | * | 2/1996 | Richardson et al. | ....... 424/94.6 |
| 5,635,462 A | | 6/1997 | Fendler et al. | ............... 510/131 |
| 5,653,970 A | * | 8/1997 | Vermeer | .................. 424/70.24 |
| 5,660,692 A | | 8/1997 | Nesburn et al. | ....... 204/157.68 |
| 5,773,249 A | | 6/2000 | Cappello et al. | ........... 435/69.1 |

FOREIGN PATENT DOCUMENTS

| JP | 51131837 | 11/1976 |
|---|---|---|
| WO | 97/00609 | 1/1997 |

* cited by examiner

*Primary Examiner*—Thurman K. Page
*Assistant Examiner*—Blessing Fubara
(74) *Attorney, Agent, or Firm*—Vidas, Arrett & Steinkra

(57) ABSTRACT

Reduced odor or odorless antimicrobial phenolic compositions containing collagen amino acids and methods of use are disclosed. The compositions can be formulated for use as a soap, emollient or hard surface cleaner. In one particularly advantageous embodiment, a composition of the invention is formulated as an antimicribial cleaner including an amount of collagen amino acids sufficient to decrease the odor of the phenolic compound below its initial levels and an amount of at least one of a soap or hard surface cleaner.

23 Claims, No Drawings

ODORLESS PHENOLIC COMPOSITIONS

FIELD OF THE INVENTION

This invention relates to reduced odor or odorless antimicrobial compositions comprising a substituted phenolic compound, and to methods for reducing the odor of the antimicrobial compositions. Further, the present invention relates to methods of using the compositions wherein microbial populations are reduced. The compositions of the present invention may be utilized in antimicrobial cleaning and antimicrobial emollient compositions.

BACKGROUND OF THE INVENTION

Compositions such as skin cleansers, lotions, and hard surface antimicrobial preparations, which possess antimicrobial properties, are widely used.

Phenol derivatives are a common class of antimicrobial agents used in antimicrobial cleaning compositions. For example, halogenated phenols, halogenated phenol homologues, hydroxybenzoic acids, and hydroxyquinolines are common antimicrobial agents used in such compositions. A specific example of a phenolic antimicrobial agent is p-chloro-m-xylenol (PCMX).

Compositions containing antimicrobial phenolic compounds however, typically have a very strong, unpleasant and undesirable odor. The undesirable odor associated with phenolic compounds is particularly disadvantageous in personal hygiene products such as lotions and skin cleansers. In order to overcome the odor problem fragrances or perfumes are frequently incorporated into the compositions. The use of fragrances or perfumes, however, increases the cost of the products containing them. Also, they are not particularly effective in masking phenolic odor and can induce allergic reactions in people sensitive to fragrances or perfumes. Typically, manufacturers of antimicrobial products such as lotions, skin cleansers or hard surface treatments emphasize the absence of phenolic based compounds in their products due to the negative association such compounds have with the consumer due to their unpleasant odor.

Consequently, a need remains for a fragrance-free antimicrobial composition wherein the odor of the phenolic based antimicrobial agent is counteracted.

Collagen amino acids are commonly used as a skin conditioner in lotions and creams. Collagen amino acids are a crude mixture of amino acids obtained by either enzymatic or alkaline hydrolysis of collagen. Collagen amino acids however, typically have an unpleasant sulfurous odor associated with them. This unpleasant odor is generally counteracted in compositions containing these collagen amino acids through the addition of fragrances of perfumes. Again, the use of fragrances or perfumes can lead to allergic reactions in people who are sensitive to them. Furthermore, the addition of such fragrances of perfumes increases the cost of the products. Therefore, a need exists for a fragrance-free means of counteracting the odor of hydrolyzed collagen amino acids as well.

SUMMARY OF THE INVENTION

This invention relates to compositions and methods which reduce the undesirable odor of antimicrobial compositions which contain phenolic compounds. Additionally, the present invention relates to methods for reducing microbial populations through the application of reduced odor antimicrobial compositions which contain phenolic compounds.

One embodiment of the present invention is an antimicrobial composition which includes an amount of collagen amino acids sufficient to decrease the odor of an antimicrobial phenolic compound and an amount of an antimicrobial phenolic based compound sufficient for reducing microbial populations.

Another embodiment of the present invention is a method for reducing the odor of a phenolic compound which includes combining the phenolic compound with an amount of collagen amino acids sufficient to decrease the odor of the phenolic compound.

A further embodiment of the present invention is a method for effectively reducing the amount of collagen amino acids used.

A further embodiment of the present invention is a method for effectively reducing the microbial population of a surface which includes contacting the surface with a composition including an antimicrobial phenolic compound and an odor reducing amount of collagen amino acids, to effectively reduce a microbial population.

The Figures and the detailed description which follow more particularly exemplify these embodiments.

DETAILED DESCRIPTIONS OF THE PREFERRED EMBODIMENTS

The present invention is directed to reduced odor or odorless antimicrobial compositions and to methods for reducing the odor of antimicrobial cleaning and antimicrobial emollient compositions. In particular, the invention relates to reduced odor or odorless phenolic compositions which include a mixture of collagen amino acids and phenolic compounds. While the present invention is not limited to the following aspects of the invention, an appreciation of the invention will be gained through the discussion provided below.

Reference herein to the term weight percent (wt-%) of any phenolic compound, collagen amino acid, or mixtures thereof in a composition is, unless otherwise specified, based on the weight of the phenolic compound or solutions thereof, or collagen amino acids or solutions thereof, present in the particular composition. For example, an antimicrobial emollient composition or a antimicrobial cleaning composition compared to the total weight of the final composition.

Reference herein to "percent solids", of any phenolic compound, collagen amino acid, or mixtures thereof in a composition is, unless otherwise specified, based on the weight of the solid substance, such as phenolic compound, compared to the total weight of a composition of the solid substance in a solvent such as water, ethanol, and so forth.

Reference herein to "phenolic compound," unless otherwise specified, refers to compounds which include one or more phenol moieties of the general formula I.

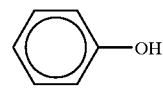

(I)

Reference herein to "collagen amino acid," unless otherwise specified, refers to amino acids obtained by hydrolysis of collagen. Typically, collagen amino acids are obtained by either enzymatic or alkaline hydrolysis of collagen.

Reference herein to "antimicrobial composition," unless otherwise specified, includes composition which are active against bacteria, fungi, yeast, protozoa, viruses, and so forth.

Reference herein to "reduced odor," unless otherwise specified, refers to the odor of a composition which is lessened in reference to the initial odor of the individual components as determined by human olfactory assessment. This is typically accomplished through the use of panel sensory evaluations.

Reference herein to "odorless," unless otherwise specified, refers to the odor of a composition which is considered nondetectable in a sensory panel evaluation in reference to the initial odor of the individual components as determined by human olfactory assessment. PCMX by itself, in contrast, has a very unpleasant odor.

A halogen is defined as one of the group VII elements of the periodic table including chlorine, bromine, fluorine and iodine.

A heteroatom is defined as nitrogen, oxygen, phosphorus, and sulfur.

Reference herein to "alkyl" unless otherwise specified, refers to $C_1$–$C_{20}$ linear or branched, saturated or unsaturated, substituted or unsubstituted hydrocarbon group. An alkyl ether group is an alkyl group containing an oxygen atom such as —$(CH_2)_n$—O— or —$(CH_2$—$CH_3$—$CH_2)_n$—O—, and an alkoxy group is an alkyl group containing an oxygen atom such as —$(CH_2CH_2O)_n$— or —$(CH_2CH(CH_3)CH_2O)_n$— where n=1 to 20, for example.

An aryl group is defined as a phenyl, benzyl, or naphthyl group containing 6 to 17 carbon atoms and in which the aromatic ring on the phenyl, benzyl or naphthyl group may be substituted with a $C_1$–$C_3$ alkyl group. An aryloxy group is aryl having an oxygen substituent such as -phenyl-O— or -benzyl-O—, for example. An aralkyl group is aryl having an alkyl substituent of 1 to 6 carbon atoms.

Reference herein to "lotion," unless otherwise specified, refers to a composition or agent which softens, smoothes, or moisturizes the skin. Agents useful for such effects, often referred to as emollients, include polyhydric alcohols such as glycerin, sorbitol, mannitol, and propylene glycol and its homopolymers; fatty acid esters of simple monohydric alcohols (i.e. an alcohol in which a hydroxyl group (—OH) has been replaced by one of the hydrogen atoms of a hydrocarbon) including isopropyl palmitate or isopropyl myristate and similar esters; polyol esters of fatty acids; ethoxylated lanolins, vegetable oils, mineral oils, and similar naturally derived compounds such as aloe; and so forth. Such compounds are known by those of skill in the art. Suitable commercial lotions compositions include Epicare® Moisturizing Lotion available from Ecolab Inc. in St. Paul, Minn.

Reference herein to "soap," unless otherwise specified, refers to a surface active agent or surfactant having a neutral to alkaline pH typically derived from neutralization of fatty acids with an alkaline compound such as alkali metal hydroxide (e.g. NaOH or KOH) or an alkanolamine (e.g. MEA, DEA or TEA). Such soaps are known to those of skill in the art and may be incorporated into skin cleanser compositions such as Suite Scrub® available from Ecolab Inc. in St. Paul, Minn.

Reference herein to "hard surface treatments," such as santizers or disinfectants, unless otherwise specified herein refers to preparations designed to reduce the microbial population of a hard surface. Hard surfaces include floors, walls, countertops, and other architectural surfaces and may be formed of materials such as ceramic, plastic, concrete, metal, brick, wood, glass and composite materials.

Hard surface sanitizers or disinfectants typically contain solvents, chelating agents, enzymes, surfactants, viscosity modifiers, fragrances, dyes, and so forth. Suitable commercial hard surface disinfectants include Martar® available from Ecolab Inc. in St. Paul, Minn.

Typically, skin cleansing agents, as well as sanitizers and disinfectants, include at least one surfactant for removal of soils. The surfactants useful herein are preferably anionic, nonionic or amphoteric, or some combination thereof.

Examples of anionic surfactants useful herein include but are not limited to soaps, sulfates, sulfonates and carboxylates such as alkyl carboxylate salts, and so forth. More specifically, useful anionic surfactants include alkyl sulfates and sulfonates, alkyl ether sulfates and sulfonates, alkyl aryl sulfates and sulfonates, aryl sulfates and sulfonates, sulfated fatty acid esters, sulfonated fatty acids, sulfated monoglycerides, sulfonated olefins, primary or secondary alkane sulfonates, alkyl sulfosuccinates, acyl taurates, methyl acyl taurates, acyl isethionates, alkyl glyceryl ether sulfonate, sulfonated methyl esters, alkyl phosphates, acyl glutamates, acyl sarcosinates, alkyl sulfoacetates, acylated peptides, alkyl ether carboxylates, acyl lactylates, anionic fluorosurfactants, ethoxylated alkyl sulfates, alkyl glyceryl ether sulfonates, fatty acyl glycinates, alpha-sulfonated fatty acids, their salts and/or their esters, alkyl ethoxy carboxylates, and so on and so forth, and mixtures thereof.

Any counter cation, M, can be used on the anionic surfactant. Preferably the counter cation is selected from the group consisting of sodium, potassium, ammonium, monoethanolamine, diethanolamine, and triethanolamine. More preferably the counter cation is ammonium.

Examples of nonionic surfactants include but are not limited to alkyl polyglycosides, alcohol ethoxylates such as fatty alcohol ethoxylates and/or propoxylates, alkyl phenolethyoxylates, glycol ester surfactants, POE(20) sorbitan monooleate, polyethylene glycol cocoate, propylene oxide/ethylene oxide block polymers, alkanolamines, and so forth.

Examples of amphoteric surfactants useful herein include but are not limited to betaines, amine oxides, sultaines, and so forth. More specifically, examples of useful amphoteric surfactants include alkyl betaines (oleyl betaine and lauryl betaine), cocamidopropyldimethyl betaine, cocamido betaine, alkyl sultaines, alkyl amphoacetates (cocamphoacetate), alkyl amphodiacetates (cocamphodiacetate), alkyl amphopropionates, alkyl amphodipropionates (cocamphocarboxypropionate), cocamphocarboxy propionic acid, cocamidopropylhydroxysultaine, alkyldimethyl amine oxides, coconut monoethanolamine, cetydimethylamine oxide, stearamine oxide, oleamine oxide, cocamidopropylamine dimethyl oxide, and so forth.

This list is not an exclusive list and is only intended as a guide. Surfactants are discussed in detail in *McCutcheon's Detergents and Emulsifiers*, 1999, North American Edition, MC Publishing Co. One of ordinary skill in the art would know how to select surfactants for use in such systems.

The surfactant system may also be composed of a combination of surfactants. For example, the surfactant system may be composed of a mixture of one or more surfactants of either the same type, or of different types. For example, anionic surfactants may be used in combination with nonionic or amphoteric surfactants. Various conventional surfactant systems are commercially available and are known to those of skill in the art.

As understood by one of ordinary skill in the art, surfactants can also interfere with the effectiveness of the PCMX, some more than others.

Viscosifiers or thickeners may also be added to the compositions of the present invention. Examples of suitable thickeners include but are not limited to cellulose derivatives (e.g., methyl cellulose and hydroxy propylmethyl cellulose), synthetic high molecular weight polymers (e.g., carboxyvinyl polymer and polyvinyl alcohol), plant hydrocolloids (e.g., karaya gum and tragacanth gum), clay thickeners (e.g., colloidal magnesium aluminum silicate and bentonite), carboxyvinyl polymers, and so forth.

Buffers may be added to the compositions of the present invention to adjust the pH. Such compounds include but are not limited to alkali metal hydrogen phosphates, hydrogen sulfate salts, sodium acetates, and so forth.

Dyes and fragrances may optionally be utilized in the compositions of the present invention, although they are not necessary to the present invention to reduce odor. Such dyes and fragrances are commercially available and known to those of skill in the art. Dyes which can be used according to the invention are disclosed in Colour Index: Pigments and Solvent Dyes: Third Edition, published by the Society of Dyers and Colourists in 1989. Suitable dyes include for example, Direct Blue 86 (Miles), Fastusol Blue (Mobay Chemical Corp.), Acid Orange 7 (American Cyanamid), Basic Violet 10 (Sandoz), Acid Yellow 23 (GAF), Acid Yellow 17 (Sigma Chemical), Sap Green (Keyston Analine and Chemical), Metanil Yellow (Keystone Analine and Chemical), Acid Blue 9 (Hilton Davis), Sandolan Blue/Acid Blue 182 (Sandoz), Hisol Fast Red (Capitol Color and Chemical), Fluorescein (Capitol Color and Chemical), Acid Green 25 (Ciba-Geigy), and the like.

Fragrances which can be used according to the invention include those disclosed in Common Fragrances and Flavour Materials: Second Edition, by VCH Publishers, published 1990. Suitable fragrances or perfumes include for example, terpenoids such as citronellol, aldehydes such as amyl cinnamaldehyde, a jasmine such as C1S-jasmine or jasmal, vanillin, and the like.

Other optional ingredients depending on the end use include abrasives, anticaking agents, antioxidants, binders, bulking agents, chelating agents, chemical additives, cosmetic astringents, cosmetic preservatives, denaturants, drug astringents, external analgesics, film formers, opacifying agents, plasticizers, preservatives, propellants, reducing agents, skin bleaching agents, foam boosters, hydrotropes, solubilizing agents, suspending agents (nonsurfactant), sunscreen agents, UV absorbers, Vitamin E, aloe, and so on and so forth. These optional ingredients are known to those of skill in the art.

The phenolic compounds useful herein those compounds which include a phenol moiety. Phenolic compounds include phenol derivatives such as, for example, phenol substituted with, for example, one or more halogen, alkyl, alkoxy, aryl, aryloxy, aralkyl, and/or hydroxy moieties. The phenolic compounds can be in the free hydroxyl form or an acceptable salt thereof such as, for example, sodium, potassium, calcium, or ammonium. Preferably the phenolic compounds function to kill or inhibit the growth of bacteria, yeast, mold, fungi, protozoa, viruses and so forth, and can be incorporated into antimicrobial compositions including those used for skin cleansing, hard surfaces and lotions. Preferred phenolic compounds include those which can be accepted for use in personal hygiene products and surface treatment antimicrobial compositions.

Examples of suitable phenolic compounds include halo phenols, preferably ortho- or para-substituted halo phenols such as o-chlorophenol; alkylhalo phenols such as p-chloro-m-xylenol; alkyl phenols such as t-amylphenol; aryl phenols such as o-phenyl phenol, and benzyl-substituted halophenols such as o-chloro-p-benzylphenol. Preferably, the phenolic compound is t-amylphenol, o-chloro-p-benzylphenol, p-chloro-m-xylenol, or o-phenyl phenol. Most preferably, the phenolic compound is p-chloro-m-xylenol (PMCX). One commercial source is NIPA Laboratories, Biocides business of BTP plc's Performance Chemicals Division, United Kingdom (Deleware, USA).

The use of phenolic compounds in combination with residual activity enhancers in various antimicrobial formulations is discussed in copending application Ser. No. 584, 447, entitled ANTIMICROBIAL COMPOSITION, incorporated by reference in its entirety herein.

The collagen amino acids useful herein are a crude mixture of amino acids obtained by either enzymatic or alkaline hydrolysis collagen. Typically, those amino acids considered collagen amino acids include: alanine, arginine, aspartic acid, cysteine, glycerine, glutamic acid, histidine, hydroxy lysine, hydroxy proline, isoluceine, luceine, lysine, methionine, phenylalanine, proline, serine, threonine, tyrosine, valine, for example. Collagen amino acids are a natural product and, therefore, the exact composition of the various amino acids in the mixture will vary.

Suitable collagen amino acid compositions include from about 0 to about 20% alanine, from about 0 to about 10% arginine, from about 0 to about 10% aspartic acid, from about 0 to about 5% cysteine, from about 0 to about 30% glycerine, from about 0 to about 20% glutamic acid, from about 0 to about 5% histidine, from about 0 to about 5% hydroxy lysine, from about 0 to about 20% hydroxy proline, from about 0 to about 5% isoluceine, from about 0 to about 5% luceine, from about 0 to about 10% lysine, from about 0 to about 5% methionine, from about 0 to about 5% phenylalanine, from about 0 to about 20% proline, from about 0 to about 5% serine, from about 0 to about 5% threonine, from about 0 to about 5% tyrosine, from about 0 to about 5% valine.

Preferable collagen amino acids include about 10% alanine, about 8% arginine, about 6% aspartic acid, about 0.1% or less cysteine, about 25% glycerine, about 10% glutamic acid, about 1% histidine, about 1% hydroxy lysine, about 13% hydroxy proline, about 2% isoluceine, about 3% luceine, about 4% lysine, about 1% methionine, about 2% phenylalanine, about 15% proline, about 3% serine, about 2% threonine, about 1% tyrosine, about 3% valine. Typically collagen amino acids include water and salt. Suitable collagen amino acids are available from Croda International Plc in East Yorkshire.

The phenolic-collagen antimicrobial compositions of the present invention are useful in skin cleansers, lotions, and in hard surface disinfectants and sanitizers.

The odor associated with phenolic compounds can be reduced or eliminated by combining collagen amino acids with the phenolic compound. The phenolic compound is combined with an amount of collagen amino acids sufficient to decrease the odor of the phenolic compound below its initial levels as determined by human olfactory assessment in a blind panel test.

Typically, the amount of collagen amino acids sufficient to decrease the odor of the phenolic compound below its initial levels is a ratio of collagen amino acids to phenolic compound of about 1:3 to about 3:1. Consequently, the compositions of the present invention include a mixture of phenolic compound and collagen amino acids in a ratio from about 1:3 to about 3:1 phenolic compound to collagen amino acids on a solids basis. For example, a phenolic-collagen antimicrobial composition used as an additive includes a mixture of phenolic compound and collagen amino acids in a ratio from about 1:3 to about 3:1 phenolic compound to collagen amino acids on a solids basis. Preferably, the ratio of phenolic compound to collagen amino acids is in the range of about 1:2 to about 2:1 and most preferably in the range of about 1:1.

As a percentage of the total composition weight, the phenolic-collagen amino acid antimicrobial compositions such as skin cleansers and lotions typically include from about 0.1 to about 50 wt-% of the composition of phenolic compound/collagen amino acid blend. In some embodiments, phenolic-collagen antimicrobial skin cleansers and lotions include from about 0.1 to about 20 wt-% of the composition of the phenolic compound/collagen amino acid blend. In preferred embodiments, the phenolic/collagen antimicrobial compositions include from about 0.1 to about 4 wt-% of the composition of the phenolic compound/collagen amino acid blend. The ratio of phenolic compound to collagen amino acids remains the same in all cases.

Hard surface antimicrobial compositions that include the phenolic compound/collagen amino acid blend of the present invention typically have from about 0.1 to about 50 wt-% of the composition of the phenolic compound/collagen amino acid blend. In some embodiments, the hard surface compositions include from about 1 to about 30 wt-% of the composition of the phenolic compound/collagen amino acid blend. In some preferred embodiments, the hard surface compositions include from about 5 to about 20 wt-% of the composition of the phenolic compound/collagen amino acid blend. Again, the ratio of phenolic compound to collagen amino acids is from 1:3 to 3:1.

An effective amount of reduced odor or odorless phenolic antimicrobial composition for use is considered to be any amount sufficient to decrease or inhibit the increase of a microbial population relative to an initial microbial population. This amount can be readily determined by one of ordinary skill in the art.

An effective amount of reduced or odorless phenolic antimicrobial composition may be determined by the degree of bacteriocidal or bacteriostatic activity required. For example an effective amount of reduced or odorless phenolic antimicrobial composition includes that which reduces a microbial population by about 10 to 25%. In one embodiment, an effective amount of reduced or odorless phenolic antimicrobial composition includes that which reduces a microbial population by about 25 to 50%. Typically, an effective amount of reduced or odorless phenolic antimicrobial composition includes that which reduces a microbial population by about 50 to 75%. In a preferred embodiment, an effective amount of reduced or odorless phenolic antimicrobial composition includes that which reduces a microbial population by about 75 to 100%. The degree to which a microbial population is reduced by the phenolic based antimicrobial compositions of the present invention may be determined by, for example, ASTM Standard Test Method E1135-87 (1987) "Efficacy of Sanitizers Recommended for Inanimate Non-food Contact Surfaces" incorporated herein by reference.

The phenolic/collagen antimicrobial compositions of the present invention find use in both commercial and domestic applications including personal hygiene compositions and hard surface treatment compositions.

For personal hygiene products, the compositions are useful for reducing the microbial populations of the skin. For use on skin, the compositions are typically found in a cleanser or lotion formulation. The formulations may include from about 0.1 to about 50 wt-% of the phenolic compound/collagen amino acids blend, preferably from about 0.1 to about 20 wt-% and most preferably from about 0.1 to about 4 wt-%.

For hard surface treatments, the compositions are useful for reducing the microbial population on walls, floors, countertops, equipment, and so forth. Such formulations find use in healthcare facilities and institutions, various commercial settings such as manufacturing or processing sites, as well as in domestic settings.

These hard surfaces disinfectants or sanitizers typically include from about 0.1 to about 50 wt-% of the phenolic compound/collagen amino acid blend, preferably from about 1 to about 30 wt-%, and most preferably from about 5 to about 20 wt-%. Again, the ratio of collagen amino acids to phenolic compound remains about 1:3 to about 3:1.

The following nonlimiting examples further illustrate the present invention, but are in no way intended as a limitation thereon.

EXAMPLES

Example 1

Effect of Ratio on Odor

A 50% solids solution of PCMX in ethanol was combined in various ratios with a 40% aqueous solution of collagen amino acids and the resulting odor noted by a panel of 13 individuals after allowing them to smell the various compositions. The odors of the various compositions detected by the individuals is summarized in Table 1.

TABLE 1

| Collagen Amino Acids (40%) | PCMX (50%) | Odor Noted |
|---|---|---|
| 100% | 0% | dirty sweat socks |
| 75% | 25% | slight amino acid |
| 50% | 50% | neutral/none |
| 25% | 75% | very slight phenolic |
| 0% | 100% | phenolic |

The data in Table 1 demonstrates that collagen amino acids reduce the phenolic odor of PCMX. Additionally, the odor of the phenolic compound is completely eliminated when specific ratios of collagen amino acids are used.

An additional unexpected benefit was the elimination of odor of the collagen amino acids.

Example 2

Effect of Amino Acid Source

Mixtures of PCMX and amino acids were prepared as above except that amino acids from hydrolyzed silk were used in place of the collagen amino acids. The odors of the resulting compositions were assessed as above. The results of these assessments are summarized in Table 2.

TABLE 2

| Silk Amino Acids (40%) | PCMX (50%) | Odor Noted |
|---|---|---|
| 100% | 0% | dirty sweat socks |
| 75% | 25% | phenolic |
| 50% | 50% | phenolic |
| 25% | 75% | phenolic |
| 0% | 100% | phenolic |

The data in Table 1 demonstrates that amino acids from silk do not reduce the phenolic odor of PCMX.

Example 3
Reduction of Odor of Other Phenolic Compounds

A mixture of phenolic compounds was prepared composed of 32.8% o-phenylphenol, 16.5% p-tert-phenol, and 50.7% o-benzyl-phenol. An equal solids amount of 40% aqueous collagen amino acid solution was added to the mixture. A panel of 13 individuals was allowed to smell the resulting composition. No odor was detected by the individuals. Thus, the mixture of phenolic compounds and collagen amino acids effectively eliminated the odor of both the amino acids and the phenolic compounds.

Example 4
Lotion Containing Reduced-Odor PCMX

A composition was prepared by mixing 2 g of 50% PCMX in ethanol with 1 g of 40% collagen amino acids. This was then added to 97.0 g of Epicare Moisturizing Lotion® (Ecolab Inc., St. Paul, Minn.). A test panel of 13 individuals was unable to detect the presence of PCMX odor in the bottle of lotion or on their hands after application of the lotion.

Example 5
Hard Surface Disinfectant Containing Reduced-Odor Phenolics

A composition was prepared by mixing 10 g of 40% aqueous collagen amino acids and 97.0 g of Matar® (Ecolab Inc., St. Paul, Minn.), a hard surface phenolic disinfectant, the mixture resulting in an elimination of the strong phenolic odor. A test panel of 13 individuals was unable to detect the presence of the strong odor associated with the phenolic compound.

Example 6
Soap Containing Reduced-Odor PCMX

A composition was prepared by mixing 0.1 g PCMX with 0.1 g of collagen amino acids in 0.1 g ethanol. This composition was then added to 9.7 g of LiquaSan® C soap available from Ecolab Inc. in St. Paul, Minn. A test panel of 13 individuals was unable to detect the presence of PCMX odor in the bottle of soap or on their hands after washing with the soap.

Example 7
Antimicrobial Affect of Compositions Containing a Phenolic Compound and Collagen Amino Acids The following lotion compositions were prepared and assessed for antimicrobial effects against *Staphylococcus aureus* and *Escherichia coli* bacteria.

1)
    7.0 g Epicare Moisturizing Lotion® (Ecolab Inc., St. Paul, Minn.),
    1.5 g PCMX, and
    1.5 g ethanol 2)
    5.5 g Epicare moist. Lotion,
    1.5 g PCMX,
    1.5 g Collagen CAA amino acids, and
    1.5 g ethanol The lotion compositions were added to suspensions of *Staphylococcus aureus* and *Escherchia coli* bacteria and the amount of bacteria killed after 1 minute was assessed. The compositions exhibited a >5 log kill in each instance. The test method used is referred to in the industry as Suspension Kill Time Study. Such a method may be found in Block S. S., *Disinfection, Sterilization, and Preservation*, Philadelphia: Lea and Febiger; 4th ed; 1991. This test method is known to those of ordinary skill in the art.

It has been discovered that antimicrobial compositions including combinations of collagen amino acids and phenolic antimicrobial compounds in a specified ratio range surprisingly do not possess odors associated with the collagen amino acids or the phenolic compounds. Additionally, the cleaning or moisturizing characteristics of such antimicrobial compositions such as soaps, emollients, and surface cleaners are not affected.

The above specification, examples and data provide a complete description of the manufacture and use of the composition of the invention. Since many embodiments of the invention can be made without departing from the spirit and scope of the invention, the invention resides in the claims hereinafter appended.

I claim:

1. An antimicrobial composition comprising collagen amino acids and an antimicrobial phenolic compound selected from halo phenols, alkyl-halo phenols, alkyl phenols, aryl-phenols, and benzyl-halo-phenols or combinations thereof in a ratio sufficient to decrease the odor of said phenolic compound.

2. The composition of claim 1, wherein said antimicrobial phenolic compound is selected from the group consisting of o-chlorophenol, p-chloro-m-xylenol, t-amylphenol, o-phenyl phenol, and o-chloro-p-benzylphenol or combinations thereof.

3. The composition of claim 1, wherein said antimicrobial phenolic compound is p-chloro-m-xylenol.

4. The composition of claim 1, wherein said collagen amino acids comprise a combination of alanine, arginine, aspartic acid, cysteine, glycerine, glutamic acid, histidine, hydroxy lysine, hydroxy proline, isoluceine, luceine, lysine, methionine, phenylalanine, proline, serine, threonine, tyrosine, valine.

5. The composition of claim 1, wherein said collagen amino acids comprise 0 to 20% alanine, about 0 to 10% arginine, 0 to 10% aspartic acid, 0 to 5% cysteine, 0 to 30% glycerine, 0 to 20% glutamic acid, 0 to 5% histidine, 0 to 5% hydroxy lysine, 0 to 20% hydroxy proline, 0 to 5% isoluceine, 0 to 5% luceine, 0 to 10% lysine, 0 to 5% methionine, 0 to 5% phenylalanine, 0 to 20% proline, 0 to 5% serine, 0 to 5% threonine, 0 to 5% tyrosine, 0 to 5% valine.

6. The composition of claim 1, wherein said collagen amino acids comprise 10% alanine, 8% arginine, 6% aspartic acid, 0.1% or less cysteine, 25% glycerine, 10% glutamic acid, 1% histidine, 1% hydroxy lysine, 13% hydroxy proline, 2% isoluceine, 3% luceine, 4% lysine, 1% methionine, 2% phenylalanine, 15% proline, 3% serine, 2% threonine, 1% tyrosine, 3% valine.

7. The composition of claim 1, wherein the ratio of antimicrobial phenolic compound to collagen amino acids is from about 1:3 to about 3:1 on a solids basis.

8. An antimicrobial composition comprising:
    a) at least one member selected from the group consisting of skin cleanser formulations, lotion formulations and hard surface treatment formulations;
    b) an amount of an antimicrobial phenolic compound selected from halo phenols, alkyl-halo phenols, alkyl phenols, aryl-phenols, and benzyl-halo-phenols or combinations thereof sufficient to achieve at least about a 1 log reduction in the microbial population on a surface; and
    c) an amount of collagen amino acids sufficient to decrease the odor of an antimicrobial phenolic compound.

9. The antimicrobial composition of claim 8 wherein said collagen amino acids and antimicrobial phenolic compound are present in a ratio of 1:3 to 3:1 on a solids weight basis and said component c) is present in the composition in an amount of about 0.1% to about 50% by weight of the composition.

10. The antimicrobial composition of claim 9 wherein component c) is present in an amount of about 0.1% to about 20% by weight of the composition.

11. The antimicrobial composition of claim 10 wherein component a) is present in an amount of about 0.1% to about 4% by weight of the composition.

12. The antimicrobial composition of claim 10 wherein said base formulation is a hard surface formulation and component c) is present in an amount of about 1% to about 30% by weight of the composition.

13. The antimicrobial composition of claim 12 wherein component c) is present in an amount of about 5% to 20 wt % by weight of the composition.

14. A method for reducing the odor of a phenolic composition comprising at least one phenolic compound selected from halo phenols, alkyl-halo phenols, alkyl phenols, aryl-phenols, and benzyl-halo-phenols or combinations thereof comprising a step of combining the phenolic compound with an amount of collagen amino acids sufficient to decrease the odor of the phenolic compound below initial levels.

15. The method of claim 14 wherein said phenolic compound and said collagen amino acids are present in a ratio of about 1:3 to about 3:1 on a solids weight basis.

16. A method for reducing a microbial population of a surface comprising contacting the surface with an effective amount of a composition to reduce a microbial population wherein the composition comprises:
   a) a mixture product of antimicrobial phenolic compound and collagen amino acids in a ratio of about 1:3 to about 3:1 on a solids basis; and
   b) at least one member selected from the group consisting of skin cleanser formulations, lotion formulations and hard surface formulations.

17. The method of claim 16 wherein component a) is present in an amount of about 0.1% to about 50% by weight of the composition.

18. The method of claim 16 wherein component a) is present in an amount of about 0.1% to about 20 wt-% by weight of the composition.

19. The method of claim 16 wherein component a) is present in an amount of about 0.1% to about 4% by weight of the composition.

20. The method of claim 16 wherein component b) is a hard surface cleaner and component a) is present in an amount of about 1% to about 30% by weight of the composition.

21. The method of claim 16 wherein component b) is a hard surface antimicrobial formulation and component a) is present in an amount of about 5% to about 20% by weight of the composition.

22. A method for reducing microbial populations of a surface comprising contacting the surface with an effective amount of a composition to reduce a microbial population comprising a phenolic compound and collagen amino acids in a ratio from 1:3 to 3:1 phenolic compound to collagen amino acids on a solids weight basis.

23. The method of claim 22 wherein said surface is selected from the group consisting of human and mammalian skin.

* * * * *